(12) United States Patent
Chin

(10) Patent No.: US 8,357,719 B2
(45) Date of Patent: Jan. 22, 2013

(54) MUSCLE RELAXANT USING NEGATIVELY CHARGED GOLD NANOPARTICLES WITH CHOLINE

(76) Inventor: Chur Chin, Seoul (KR)

( * ) Notice: Subject to any disclaimer, the term of this patent is extended or adjusted under 35 U.S.C. 154(b) by 553 days.

(21) Appl. No.: 12/531,875

(22) PCT Filed: Nov. 22, 2007

(86) PCT No.: PCT/KR2007/005897
§ 371 (c)(1),
(2), (4) Date: Sep. 17, 2009

(87) PCT Pub. No.: WO2009/001994
PCT Pub. Date: Dec. 31, 2008

(65) Prior Publication Data
US 2010/0087522 A1     Apr. 8, 2010

(30) Foreign Application Priority Data
Jun. 25, 2007    (KR) .................. 10-2007-0061943

(51) Int. Cl.
*A01N 55/02* (2006.01)
*A01N 55/06* (2006.01)
*A61K 31/31* (2006.01)
*C07F 1/00* (2006.01)
*C22C 5/02* (2006.01)
*C01G 3/00* (2006.01)
*C01G 5/00* (2006.01)
*C01G 7/00* (2006.01)
*C22B 11/00* (2006.01)
*C22B 15/00* (2006.01)

(52) U.S. Cl. ........ 514/495; 514/497; 556/110; 420/507; 423/23

(58) Field of Classification Search .................. 514/495, 514/497; 556/110; 420/507; 423/23
See application file for complete search history.

(56) References Cited

U.S. PATENT DOCUMENTS 7,160,525 B1 * 1/2007 Peng et al. ................... 423/1
2006/0222595 A1 10/2006 Mukherjee et al. .......... 424/9.34

FOREIGN PATENT DOCUMENTS

| EP | 18550 A2 * | 11/1980 |
| JP | 2007-127620 | 5/2007 |
| WO | 2006/008742 | 1/2006 |

OTHER PUBLICATIONS

Wang et al., "Fabrication of layer-by-layer modified multilayer films containing choline and gold nanoparticles and its sensing application for electrochemical determination of dopamine and uric acid," *Talanta* 73: 431-437, 2007.

Xiao et al., "An $Os^{11}$-Bisbipyridine-4-Picolinic Acid Complex Mediates the Biocatalytic Growth of Au Nanoparticles: Optical Detection of Glucose and Acetylcholine Esterase Inhibition," *Chem. Eur. J. 11*: 2698-2704, 2005.

* cited by examiner

*Primary Examiner* — Sreeni Padmanabhan
*Assistant Examiner* — Sarah Pihonak
(74) *Attorney, Agent, or Firm* — The Webb Law Firm

(57) ABSTRACT

A drug having a muscle relaxing effect can be prepared by binding negatively charged gold nanoparticles having a size of 1.4 nm fitted to synaptic clefts to choline through ionic bonds, thereby inducing gold-sulfur bonds in the Cys loop of an acetylcholine receptor in neuromuscular junction, and thus blocking the electric current induced in signal transduction from a nerve to a muscle, thereby blocking neuromuscular transmission chemically and physically. When the reverse is administered after surgery, the gold-sulfur bonds are broken due to the re-flow of the electric current, and thus the gold nanoparticles are again released and metabolized into neuromuscular junction. Further, such muscle relaxing effect can be applied as an anticonvulsant.

4 Claims, 3 Drawing Sheets

Ionic bonds between choline and nanoparticle

Figure 1:
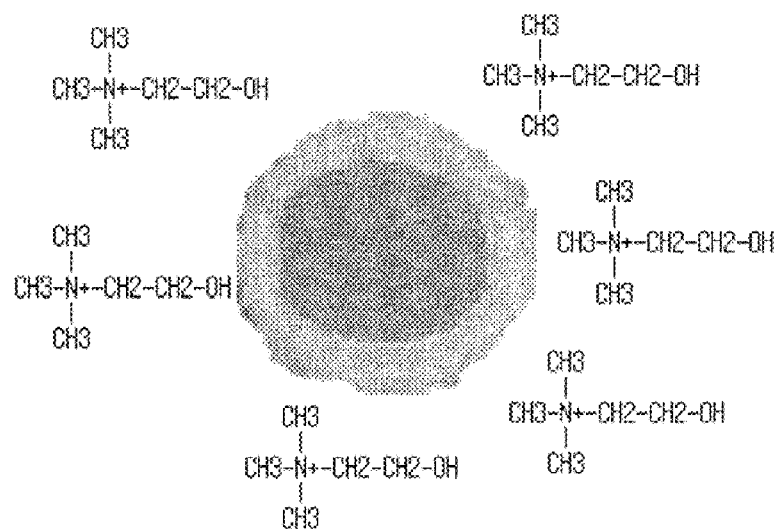
Figure 2:
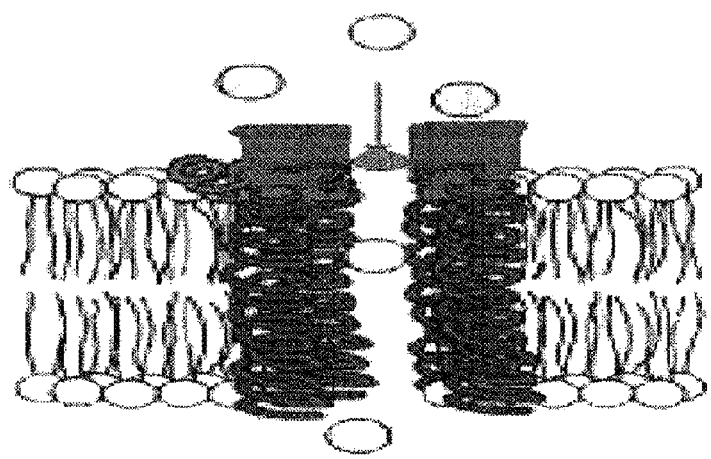
Figure 3:
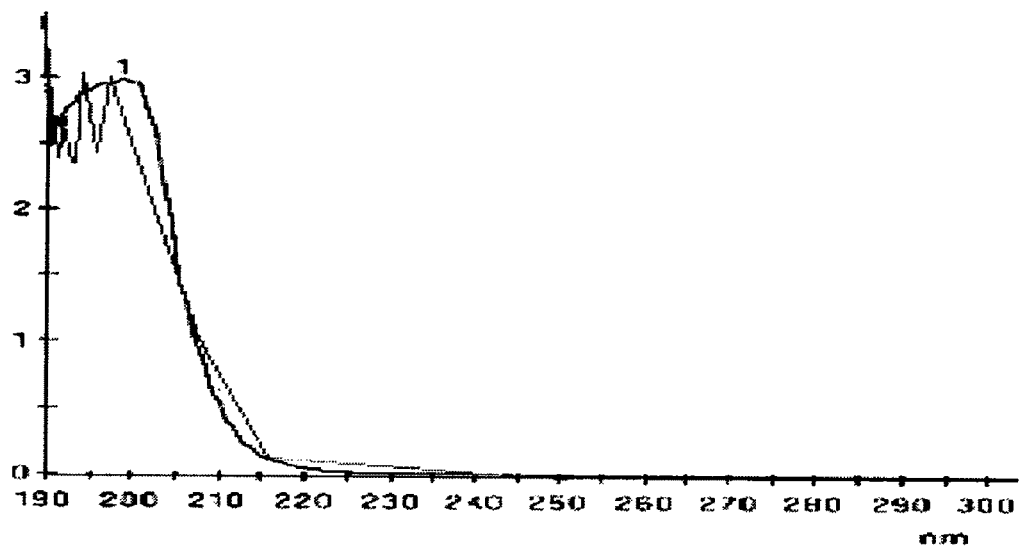
Figure 4:
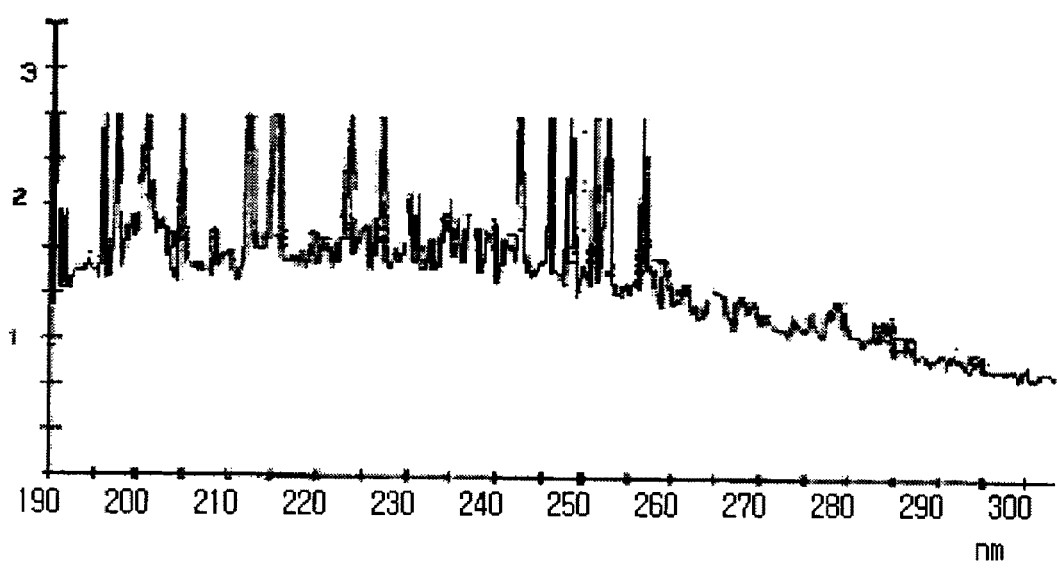
Figure 5:
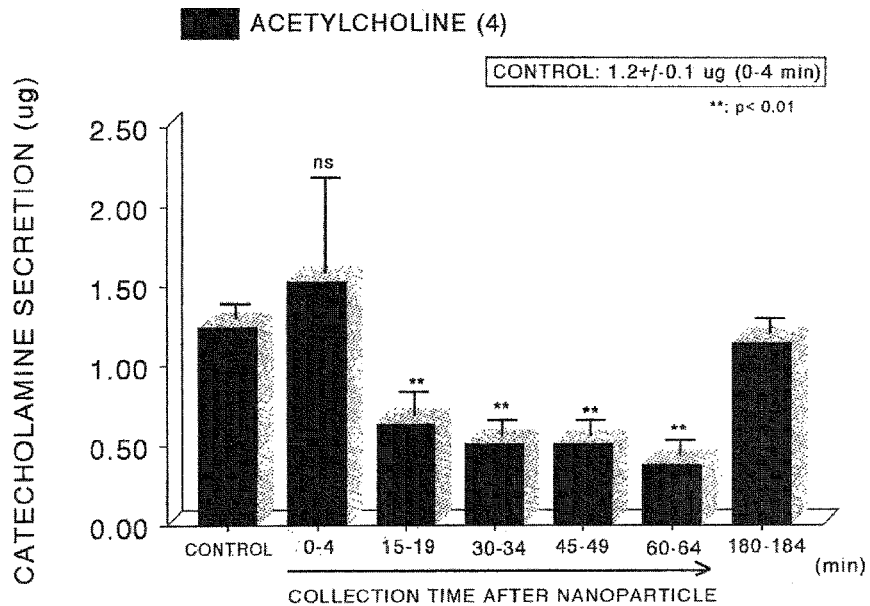
Figure 6:
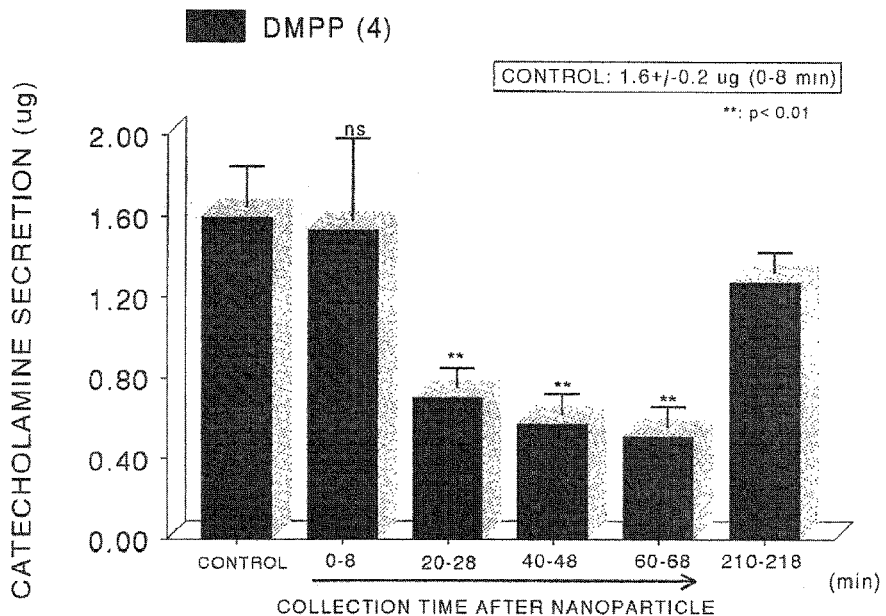

Schematic view of mechanism that choline-nanoparticle complexes act

Analysis results for choline and nanoparticles by UV VIS spectrophotometry

Analysis results for choline-nanoparticle complexes by UV VIS spectrophotometry

Effect of choline-nanoparticle complexes over time in experiment employing Ach

Effect of choline-nanoparticle complexes over time in experiment employing DMPP

US 8,357,719 B2

MUSCLE RELAXANT USING NEGATIVELY CHARGED GOLD NANOPARTICLES WITH CHOLINE

BACKGROUND OF THE INVENTION

1. Field of the Invention

Choline is a kind of vitamin B complex, and acts as a partial agonist for acetylcholine, a neurotransmitter, in neuromuscular junction. Negatively charged gold particles are formed by adhering alkaline $COO^-$ particles to a thin film of gold nanoparticles. When the negatively charged gold particles form ionic bonds with choline and then the resulting complexes are injected intravenously, the complexes migrate to an acetylcholine receptor in neuromuscular junction of a patient within 1 minute, and the choline binds to an acetylcholine-binding site thereby forming ionic bonds. The migrated nanoparticles enter the extracellular vestibule of the receptor together with a high concentration of the choline and migrate to a cysteine loop to thereby bind to the SH groups of the cysteine due to the strong binding force of gold-sulfur ions, and subsequently prevent from forming alpha subunit S=S bonds thereby blocking a flow of electric current through open ion gates. Accordingly, it is anticipated that the choline-gold nanoparticle complexes will perform a role of blocking the signal transmission in neuromuscular junction more strongly.

Since the action of cholinesterase is inhibited if reverse is administered, acetylcholine is not degraded and the acetylcholine bound to the receptor induces S═S reducing bonds in the cysteine loop. The negatively charged gold nanoparticles are come out of the ionic paths by repulsion since the gold-sulfur binding force is released due to the electric current generated by the reducing bonds.

2. Description of the Related Art

The signal transduction at neuromuscular junction is achieved by chemical means such as a neurotransmitter, or physical means such as an ionic path. Prior muscle relaxant is chemical means that blocks neuromuscular transmission since it has a similar structure to acetylcholine, a neurotransmitter, and thus binds competitively to acetylcholine and its receptor. If a method of blocking the flow and maintenance of electric current at ionic paths by using gold nanoparticles having a negative charge is used in combination with the prior means, the effect of muscle relaxing will be doubled. Further, such strong muscle relaxing effect can be applied as an anti-convulsant.

SUMMARY OF THE INVENTION

Choline

Choline is a vitamin B complex having 2-hydroxy-N,N,N-trimethylethanaminium structure, and passes through the cerebrovascular barriers. It takes only 1-2 msec for acetylcholine isolated from a presynaptic terminal to work on the postsynaptic membrane. Once a postsynaptic stimulant voltage is generated, acetylcholine is hydrolyzed into choline and acetate by cholinesterase. The choline and acetate are re-synthesized into acetylcholine by choline acetylase and are used.

Signal Transduction at Neuromuscular Junction

A neurotransmitter in a synaptic vesicle is released by a nerve impulse transmitted from a cell body to an axon terminal. As the nerve impulse reaches a cell membrane of a terminal bouton along the axon, a calcium ($Ca^{++}$) channel present in the location is opened, and calcium ions enter the terminal bouton, and the membrane of the synaptic vesicle is fused with the cell membrane.

When a presynaptic cell membrane is fused to the synaptic vesicle, the neurotransmitter in the synaptic vesicle is released into synaptic clefts and binds to a receptor present in a postsynaptic cell membrane. The receptor acts as a kind of a ligand-sensitive ion channel. The channel is an ion channel that is opened by coupling with a ligand, i.e., the neurotransmitter. When a cation channel such as a sodium channel or a calcium channel is opened, a cation that was present in extracellular fluid enters the postsynaptic portion, and thus the voltage inside the cell that has maintained a stable membrane electric potential (−80 mV) is partially changed. As the voltage reaches a threshold (−70 mV), a voltage-sensitive sodium channel is opened and a large quantity of the sodium ions in the extracellular fluid come inside the cell, and accordingly depolarization occurs thereby reversing the membrane electric potential of this portion. As the membrane electric potential is changed like this, a voltage sensitive potassium channel is now opened. As potassium ions come outside the cell, the membrane electric potential returns to its original status.

The sodium and potassium ions in which the outside and inside of the cell are reversed from the original status are exchanged in 1:1 ratio by a sodium/potassium ($Na^+/K^+$) exchange pump. At this time, energy is needed.

When the ion exchange is completely finished, the membrane electric potential returns to the original status and the membrane again becomes capable of responding to a stimulus.

The sodium ions enter a specific portion of a cell and depolarize not only the portion but also are diffused along an axon and depolarize the adjacent portion. If the diffusion occurs toward a cell body, the sodium channel is inactivated and thus an impulse is not continuously transmitted. However, if the sodium ions are diffused toward the synaptic terminal of the axon, the adjacent portion of the membrane is depolarized and the active electric potential is also generated at this portion.

Structure of an Acetylcholine Receptor

A nicotinic acetylcholine receptor is an ionic receptor controlling the ionic path in a cell membrane through a ligand. The nicotinic acetylcholine receptor consists of five subunits, and each subunit is very similar in structure. An acetylcholine receptor of a muscle consists of two α subunits and β, γ and δ subunits. The site binding with the receptor in a muscle is outside α subunits near N termini. If acetylcholine binds to the site, the α subunits become more similar to other subunits in structure, and thus the ionic path becomes more symmetrical and is opened to a size of about 0.65 nm.

The nicotinic acetylcholine receptor has a similar structure to a muscle receptor on signal transduction in a nerve. When acetylcholine binds continuously to the site, the ionic path maintains its open state. As the ionic path is opened, ions having a positive charge, particularly sodium and calcium ions, enter inside the cell.

$Na^+$ and $K^+$ are all penetrable to the nicotinic acetylcholine receptor, and in a certain site, $Ca^{2+}$ is also penetrable. $Na^+$ and $K^+$ penetrate an open site of the ionic path, and this process occurs by the change in the structure of each subunits.

It is known that the nicotinic acetylcholine receptor consists of extracelluar, transmembrane and intracellular domains (ICD) from research through Gaussian Network Model (GNM) and Anisotropic Network Model (ANM). The opening and closing of the ionic path are determined by symmetrical 3-dimensional twisting movement and asymmetrical tilting movement between each subunit. At this time, the pore size between paths is determined by the opening and closing of the disulfide (S═S) bond of cysteine (Cys) loop in and between subunits. Accordingly, if gold nanoparticles having a negative charge interrupt the disulfide bond of Cys loop between each subunit, the flow and maintenance of the electric current to the neuromuscular junction site can be blocked.

BRIEF DESCRIPTION OF THE DRAWINGS

FIG. 1 illustrates schematically a structure in which ionic bonds are formed between choline having a positive charge and a nanoparticle having a negative charge;

FIG. 2 illustrates schematically a process that choline injected intravenously after forming ionic bonds with gold nanoparticles having a similar structure to acetylcholine binds to an amino acid of a binding site on an acetylcholine receptor, and the nanoparticles, in which the ionic bonds are disrupted, bind to the SH groups of Cys loop by repulsion to the binding site having a negative charge;

FIG. 3 illustrates the analysis results for choline and nanoparticles by UV spectrophotometry, showing that the light-absorbing configurations of the choline and the nanoparticles were similarly achieved; and FIG. 4 illustrates the analysis results for choline-nanoparticle complexes by UV spectrophotometry, showing that the ionic bonds between the choline and the nanoparticles were smoothly formed by confirming the intensity and the light-absorbing region of the choline-nanoparticle complexes were more extended than those of the respective single molecules;

FIG. 5 is a graph illustrating the effect of choline-nanoparticle complexes over time in an experiment employing Ach, and schematically depicting a process that immediate reversal is achieved with the receptor inactivation effect of about 75% over time; and FIG. 6 is a graph illustrating the effect of choline-nanoparticle complexes over time in an experiment employing DMPP, and schematically depicting a process that immediate reversal is achieved with the receptor inactivation effect of about 75% over time.

DETAILED DESCRIPTION OF THE INVENTION

Firstly, ionic bonds are induced by vortexing and pipetting choline having a positive charge and gold nanoparticles having a negative charge for one hour. The degree of binding is determined through the wavelength analysis by UV VIS spectrophotometry.

FIG. 1 illustrates ionic bonds between 1 mM choline and 30 nM negatively charged nanoparticle: the configuration that $COO^-$ groups coated on a thin film of the nanoparticle binds to $N^+$ groups of the choline molecules is schematically illustrated.

FIG. 2 illustrates schematically the binding site of choline and gold nanoparticles having a negative charge on a nicotinic acetylcholine receptor at a neuromuscular junction postsynaptic muscle cell. The red color depicts the extracellular domain of the receptor, the violet color depicts the terminal of the choline molecule binding on the receptor, the blue color depicts transmembrane and intracellular domains, and the pale blue color depicts sodium and calcium ions passing through an ionic path. When choline-nanoparticle Complexes bind strongly to the receptor, the gold nanoparticle molecules are detached from the binding body by repulsion and block the flow of the ionic path through adsorption of the SH groups inside a glycoprotein receptor.

FIG. 3 illustrates the analysis results for choline and gold nanoparticles having a negative charge by UV VIS spectrophotometry. The black graph depicts the analysis results for the choline, and the red graph depicts those for the gold nanoparticles having a negative charge by UV VIS spectrophotometry. It was confirmed that the absorbance of the two molecules was achieved in a similar degree within almost the same wavelength range. The used apparatus was Shimadzu UV3101PC made in Japan. The measurement was made in a light absorbing mode in the UV wavelength range of 190 to 300 nm, and the resolution was possible to 0.1 nm.

FIG. 4 illustrates the analysis results for complexes of the choline and the gold nanoparticles having a negative charge by UV VIS spectrophotometry, and shows an intensity stronger and a light absorbing range in a wavelength region wider than the absorbance of the respective molecules. The used apparatus was Shimadzu UV3101PC made in Japan. The measurement was made in a light absorbing mode in the UV wavelength range of 190 to 300 nm, and the resolution was possible to 0.1 nm.

Organ Model Experiment

The left adrenal of a Sprague-Dawley white rat was removed and cannulated according to the Wakade method, and then it was extirpated and immobilized to a leucite chamber, and an experiment was performed while perfusing with Krebs fluid.

A single injection of ACh ($5.32\times10^{-3}$ M) was treated in 0.05 ml of a buffer solution containing 137.5 mM NaCl, 2.5 mM KCl, 2 mM $CaCl_2$, 1 mM $MgCl_2$ and 10 mM D-glucose at room temperature for 3 minute. Then, the amperometric current generated by the secreted catecholamine was measured by employing an 8-μm-diameter carbon electrode. Data was computerized with IGOR software and the buffer solution was perfused every two seconds.

The agonistic effect of the choline was confirmed with a control experiment employing 1,1-dimethyl-4-phenylpiperazinium iodide (DMPP), the choline-nanoparticle complexes were treated again for 3 minutes, and then the change in the catecholamine secretion was measured.

Finally, 10 μM DMPP stimulation was performed for 2 seconds as reverse, thereby confirming whether catecholamine secretion was restarted, and verifying whether the choline-nanoparticle complexes were released from the ionic path.

Result

FIG. 5 illustrates the effect of the choline-nanoparticle complexes over time. When 0.05 ml of a single injection of ACh ($5.32\times10^{-3}$ M) was evoked in a rat adrenal gland, the receptor activation was confirmed after 15 minutes, and then when the choline-nanoparticle complexes were treated, it was confirmed that the catecholamine secretion was decreased to about 75% after 60 minutes. When ACh was again treated after about 1.5 hours, it was confirmed that immediate reversal was achieved. *: $P<0.01$.

FIG. 6 illustrates the results of an experiment for the effect of the choline-nanoparticle complexes employing DMPP over time. When a single injection of DMPP was evoked in a rat adrenal gland, the receptor activation was confirmed after 15 minutes, and then when the choline-nanoparticle complexes were treated, it was confirmed that the catecholamine secretion was decreased to about 75% after 60 minutes. When DMPP was again treated after about 3.5 hours, it was confirmed that immediate reversal was achieved. *: $P<0.01$.

By binding gold nanoparticles to choline through ionic bonds, a drug having a stronger muscle relaxing effect obtained by blocking physically other ionic paths than prior muscle relaxants competitively inhibiting a receptor-ligand binding can be developed. Further, the complexes can be applied as a therapeutic agent for epilepsy.

The invention claimed is:

1. A method of providing a muscle relaxant effect in a subject, comprising administering to a subject, choline-gold nanoparticle complexes, said complexes formed from ionic bonding between negatively charged gold nanoparticle and choline.

2. The method of claim 1, wherein the gold nanoparticle is coated by $COO^-$ on a thin film of the gold nanoparticle.

3. The method of claim 1, wherein the choline-gold nanoparticle complexes comprise 2-5 moles of gold nanoparticle per $10^5$ moles of choline.

4. The method of claim 1, wherein the choline-gold nanoparticle complexes bind to acetylcholine receptors of a muscle in a subject and the gold nanoparticles of the choline-gold nanoparticle complexes bind to SH groups of the receptor, thereby blocking neurotransmittance in a neuromuscular junction of the muscle of a subject.

* * * * *